(12) United States Patent
Ikeya et al.

(10) Patent No.: US 9,573,920 B2
(45) Date of Patent: Feb. 21, 2017

(54) COMPOUND, MEDICINE, ANTI-INFLAMMATORY, COSMETIC, FOOD AND DRINK, AND METHOD FOR PRODUCING COMPOUND

(71) Applicant: Amino Up Chemical Co., Ltd., Sapporo-shi, Hokkaido (JP)

(72) Inventors: Yukinobu Ikeya, Kusatsu (JP); Mikio Nishizawa, Kusatsu (JP); Takehito Miura, Sapporo (JP)

(73) Assignees: AMINO UP CHEMICAL CO., LTD, Sapporo-Shi, Hokkaido (JP); THE RITSUMEIKAN TRUST, Kyoto-Shi, Kyoto (JP)

(*) Notice: Subject to any disclaimer, the term of this patent is extended or adjusted under 35 U.S.C. 154(b) by 0 days.

(21) Appl. No.: 14/915,490

(22) PCT Filed: Mar. 5, 2014

(86) PCT No.: PCT/JP2014/055647
§ 371 (c)(1),
(2) Date: Feb. 29, 2016

(87) PCT Pub. No.: WO2015/029473
PCT Pub. Date: Mar. 5, 2015

(65) Prior Publication Data
US 2016/0207901 A1 Jul. 21, 2016

(30) Foreign Application Priority Data
Sep. 2, 2013 (JP) .................................. 2013-181052

(51) Int. Cl.
C07D 311/32 (2006.01)
C07D 311/40 (2006.01)
(Continued)

(52) U.S. Cl.
CPC .............. C07D 311/32 (2013.01); A23L 2/52 (2013.01); A23L 33/10 (2016.08); A61K 8/498 (2013.01);
(Continued)

(58) Field of Classification Search
CPC .... A61Q 19/00; A61K 8/498; A61K 2800/10; A23L 1/30; A23V 2002/00; C07D 311/32; C07D 311/16; C07D 311/40
See application file for complete search history.

(56) References Cited

U.S. PATENT DOCUMENTS 5,665,365 A * 9/1997 Bombardelli .......... A61K 8/498
424/401

FOREIGN PATENT DOCUMENTS

JP H06-062795 A 3/1994
JP H06-293652 A 10/1994
(Continued)

OTHER PUBLICATIONS

Witaicenis et al., Chemico-Biological Interactions, (2010), 186, p. 211-218.*
(Continued)

Primary Examiner — Yong Chu
(74) Attorney, Agent, or Firm — Enshan Hong; VLP Law Group LLP

(57) ABSTRACT

A compound is represented by Formula (I) or (II) described below.

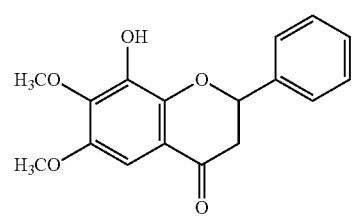

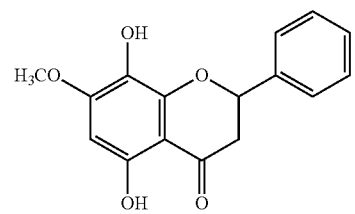

A medicine includes, as an active ingredient, a compound represented by Formula (I), (II), or (III) described below.

(Continued)

-continued

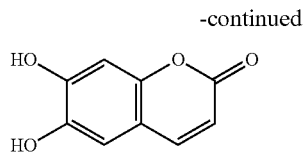

(III)

2 Claims, 6 Drawing Sheets

(51) Int. Cl.
| | |
|---|---|
| *C07D 311/16* | (2006.01) |
| *A23L 2/52* | (2006.01) |
| *A61K 8/49* | (2006.01) |
| *A61Q 19/00* | (2006.01) |
| *A61K 36/535* | (2006.01) |
| *A61K 8/97* | (2006.01) |
| *A61K 31/352* | (2006.01) |
| *A61K 31/37* | (2006.01) |

(52) U.S. Cl.
CPC ............... *A61K 8/97* (2013.01); *A61K 31/352* (2013.01); *A61K 31/37* (2013.01); *A61K 36/535* (2013.01); *A61Q 19/00* (2013.01); *C07D 311/16* (2013.01); *C07D 311/40* (2013.01); *A23V 2002/00* (2013.01); *A61K 2800/10* (2013.01)

(56) References Cited

FOREIGN PATENT DOCUMENTS

| JP | H07-215884 A | 8/1995 |
|---|---|---|
| JP | H09-000201 A | 1/1997 |
| JP | 2001-136931 A | 5/2001 |

OTHER PUBLICATIONS

Horig et al. Journal of Translational Medicine 2004, 2(44), p. 1-8.*
Schafer et al. Drug Discovery Today, 2008, 13 (21/22), 913-916.*
Takehito Miura, Kentaro Kitadate; Aroma Research No. 42 (vol. 11/No. 2, 2010) pp. 28-31 (English abstract is attached).
Yukinobu Ikeya, and others, "Hydrophobic Constituents in Perilla Extract Inhibit Production of Nitric Oxide in Rat Hepatocytes"; Abstract of the 20th International Congress on Nutrition and Integrative Medicine (ICNIM 2012) (held in Jul. 2012).
Nao Yoshinaka, and others, "Study on Active Ingredient for Inhibition of NO Production in Green Perilla"; Abstract of the 59th Annual Meeting of the Japanese Society of Pharmacognosy (held in Sep. 2012).
Liu, S. et al, Effect of esculetin on osteoarthritis in rabbit, Wuhan Daxue Xuebao (Yixue Ban), 2004, vol. 25, No. 5, pp. 567-570 (English abstract is attached).
Yang, J., Inhibitory effect of esculetin on the inducuble nitricoxide synthase expression in TNF-stimulated 3T3-L1 adipocytes, Korean Journal of Physiology & Pharmacology, 2003, vol. 7, No. 5, pp. 283-287.
Tada, M. et al, Novel antioxidants isolated from *Perilla frutescens* Britton var. crispa (Thunb.), Bioscience, Biotechnology, and Biochemistry, 1996, Vol. 60, No. 7, pp. 1093-1095.
Jakupovic, J. et al, Twenty-one acylphloroglucinol derivatives and further constituents from South African *Helichrysum* species, Phytochemistry, 1989, Vol. 28, No. 4, pp. 1119-1131.

* cited by examiner

COMPOUND, MEDICINE, ANTI-INFLAMMATORY, COSMETIC, FOOD AND DRINK, AND METHOD FOR PRODUCING COMPOUND

PRIORITY CLAIM

This is a U.S. national stage of application No. PCT/JP2014/055647, filed on Mar. 5, 2014. Priority is claimed on the following applications: Country: Japan, Application No.: 2013-181052, Filed: Sep. 2, 2013), the content of which is incorporated here by reference

TECHNICAL FIELD

The present disclosure relates to a compound, a medicine, an anti-inflammatory agent, a cosmetic, a food or drink, and a method for producing a compound.

BACKGROUND ART

In recent years, the number of patients with allergic diseases such as atopic dermatitis, contact dermatitis, and pollinosis has increased. For methods for treating such allergic diseases, symptomatic therapies have been greatly resorted to, and anti-inflammatory drugs and/or the like have been commonly used for the purpose of suppressing inflammation due to allergy.

*Perilla frutescens* Britton, which is an annual herb belonging to the family Lamiaceae and is considered to be native to southern China, has been widely cultivated in temperate regions in the Orient. In the Orient, *Perilla frutescens* Britton has been used in folk remedies since olden times, and has also been prescribed as a Chinese medicine. In Japan, *Perilla frutescens* Britton has also been used as a flavor for a food since around the Heian period.

Lamiaceae plants or ingredients originated from Lamiaceae plants have been reported to have the action of suppressing allergy and inflammation.

Patent Literature 1 discloses an antiallergic food comprising an oil or fat, and a perilla leaf extract as active ingredients. Further, Patent Literature 2 discloses an antiallergic cosmetic composition blended with an extract from the stem and leaf of a Lamiaceae plant. Further, Patent Literature 3 discloses a food for inflammatory bowel disease, comprising a highly unsaturated fatty acid and a *perilla* leaf extract as active ingredients. Further, Patent Literature 4 discloses a liquid *perilla* extract that has TNF production inhibitory action and that is effective for improvement of allergy. Further, Non Patent Literature 1 describes that rosmarinic acid, luteolin, and apigenin obtained by extracting perilla leaves contribute to the anti-inflammatory action of a perilla leaf extract. Further, Non Patent Literature 2 and Non Patent Literature 3 disclose that methyl rosmarinate and negletein originated from an extract from green perilla have NO production inhibitory action.

CITATION LIST

Patent Literature

Patent Literature 1: Unexamined Japanese Patent Application Kokai Publication No. H6-62795
Patent Literature 2: Unexamined Japanese Patent Application Kokai Publication No. H6-293652
Patent Literature 3: Unexamined Japanese Patent Application Kokai Publication No. H9-201
Patent Literature 4: Unexamined Japanese Patent Application Kokai Publication No. H7-215884

Non Patent Literature

Non Patent Literature 1: Takehito Miura, Kentaro Kitadate; AROMA RESEARCH No. 42 (Vol. 11/No. 2, 2010) pp. 28-31
Non Patent Literature 2: Yukinobu Ikeya, and others, "Hydrophobic Constituents in Perilla Extract Inhibit Production of Nitric Oxide in Rat Hepatocytes"; Abstract of the 20th International Congress on Nutrition and Integrative Medicine (ICNIM 2012) (held in July, 2012)
Non Patent Literature 3: Nao Yoshinaka, and others, "Study on Active Ingredient for Inhibition of NO Production in Green Perilla"; Abstract of the 59th Annual Meeting of the Japanese Society of Pharmacognosy (held in September, 2012)

SUMMARY OF INVENTION

Technical Problem

There have been instances in which it has been expected to identify a novel ingredient having more potent anti-inflammatory action in a Lamiaceae plant.

The present inventors found that a novel compound in a Lamiaceae plant has anti-inflammatory action, and the present disclosure was thus accomplished. An objective of the present disclosure is to provide a compound, a medicine, an anti-inflammatory agent, a cosmetic, and a food or drink which have excellent anti-inflammatory action, and a method for producing the compound.

Solution to Problem

In order to achieve the above-described objective, a compound according to a first aspect of the present disclosure is represented by Formula (I) or (II) described below:

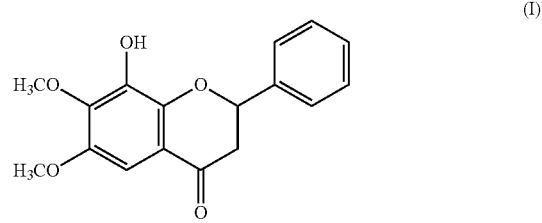

(I)

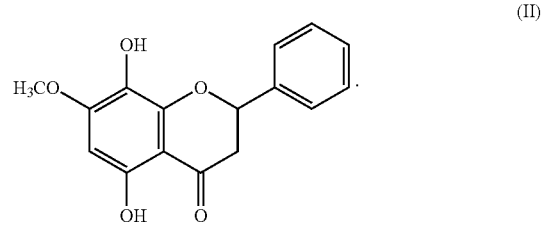

(II)

A medicine according to a second aspect of the present disclosure includes, as an active ingredient, a compound represented by Formula (I), (II), or (III) described below:

(I)

(II)

(III)

An anti-inflammatory agent according to a third aspect of the present disclosure includes, as an active ingredient, a compound represented by Formula (I), (II), or (III) described below:

(I)

(II)

(III)

A cosmetic according to a fourth aspect of the present disclosure includes a compound represented by Formula (I), (II), or (III) described below:

A food or drink according to a fifth aspect of the present disclosure includes a compound represented by Formula (I), (II), or (III) described below:

(I)

(II)

(III)

A compound according to a sixth aspect of the present disclosure, represented by Formula (I), (II), or (III) described below:

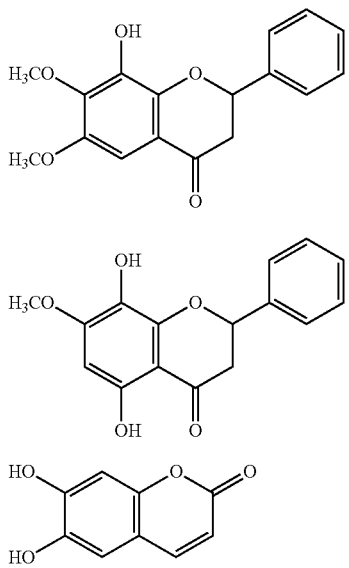

(I)
(II)
(III)

is obtained by performing extraction processing of a Lamiaceae plant.

A method for producing a compound represented by Formula (I), (II), or (III) described below:

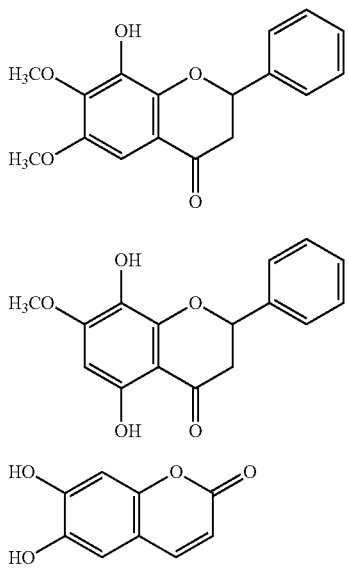

(I)
(II)
(III)

according to a seventh aspect of the present disclosure includes:

a step of performing extraction processing of a Lamiaceae plant.

Advantageous Effects of Invention

In accordance with the present disclosure, there can be provided a compound, a medicine, an anti-inflammatory agent, a cosmetic, and a food or drink which have excellent anti-inflammatory action, and a method for producing the compound.

DESCRIPTION OF EMBODIMENTS

Figure 1:
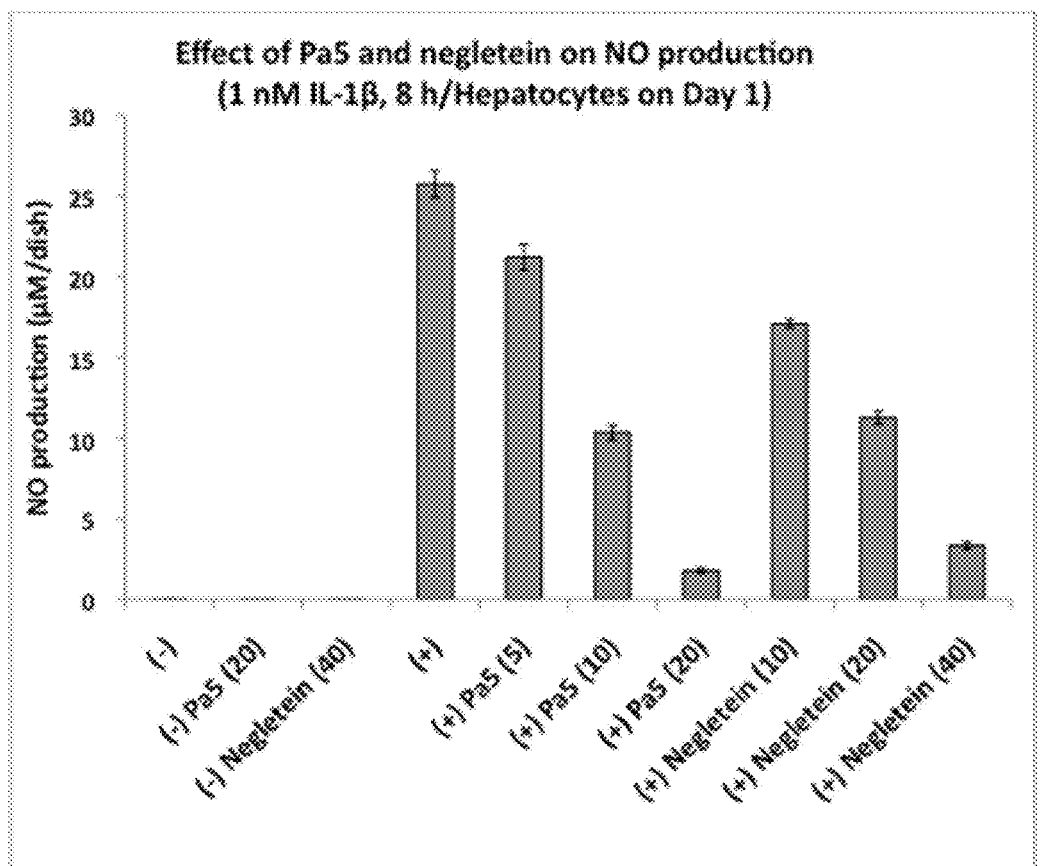
FIG. 1 is a view showing the results of measurement of NO productions.

Embodiments of the present disclosure will be described in detail below.

A compound represented by a structural formula in the present specification encompasses various stereoisomers such as tautomers, geometrical isomers, and optical isomers of the compound, and mixtures thereof (including racemic mixtures) unless a stereo structure or the like is particularly shown in the structural formula in the present specification.

First, a compound according to the present disclosure will be described.

The novel compound according to the present disclosure is a flavonoid compound and is represented by Formula (I) or (II) described below.

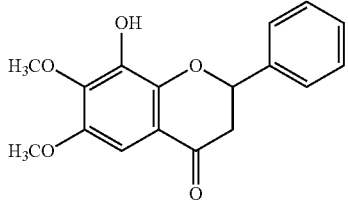

8-hydroxy-6,7-dimethoxyflavanone (Pa5)

(I)

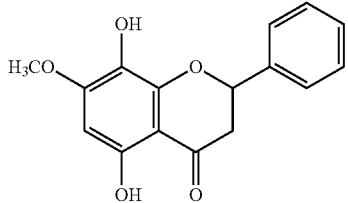

5,8-dihydroxy-7-methoxyflavanone (Pa5')

(II)

The compound represented by Formula (I) is 8-hydroxy-6,7-dimethoxyflavanone and is a novel flavonoid compound. In the present specification, the compound represented by Formula (I) may be referred to as Pa5.

The compound represented by Formula (II) is 5,8-dihydroxy-7-methoxyflavanone and is a novel flavonoid compound. In the present specification, the compound represented by Formula (II) may be referred to as Pa5'.

Pa5 and Pa5' have excellent anti-inflammatory action as described later in Examples. Thus, Pa5 and Pa5' can be used as anti-inflammatory agents in treatment of inflammatory diseases such as atopic dermatitis, contact dermatitis, pollinosis, rheumatism, and inflammatory bowel disease, as well as can be used as cosmetics and foods or drinks, as described later.

Next, a compound according to the present disclosure, obtained by performing extraction processing of a Lamiaceae plant, will be described.

The compound according to the present disclosure, obtained by performing the extraction processing of a Lamiaceae plant, is represented by Formula (I), (II), or (III) described below.

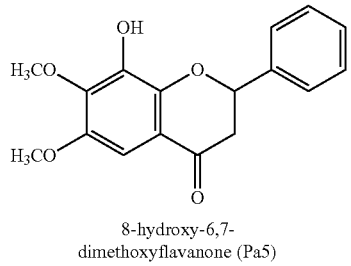

8-hydroxy-6,7-dimethoxyflavanone (Pa5)

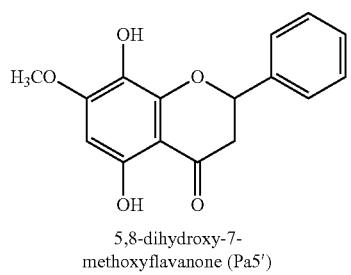

5,8-dihydroxy-7-methoxyflavanone (Pa5')

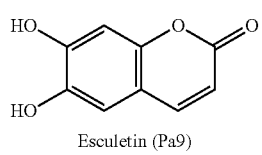

Esculetin (Pa9)

The details of the extraction processing of a Lamiaceae plant will be described later.

The compounds (Pa5 and Pa5') represented by Formulae (I) and (II) are as described above. The present inventors first found that Pa5 and Pa5' can be obtained by performing extraction processing of a Lamiaceae plant.

The compound represented by Formula (III) is esculetin. The present inventors first found that esculetin is obtained by performing extraction processing of a Lamiaceae plant and has anti-inflammatory action. In the present specification, the compound represented by Formula (III) may be referred to as Pa9.

Pa5, Pa5', and Pa9 are considered to be present as glycosides such as glucoside and glucuronide in Lamiaceae plants. It is considered that in the case of oral intake of the glycosides of Pa5, Pa5', and Pa9, sugar components are cleaved by an enzyme (β-glucosidase, glucuronidase, or the like), and Pa5, Pa5', and Pa9 in the form of aglycon migrate into blood and exert action in the body.

Pa5, Pa5', and Pa9 have excellent anti-inflammatory action as described in Examples later. Thus, Pa5, Pa5', and Pa9 can be used as anti-inflammatory agents in treatment of inflammatory diseases such as atopic dermatitis, contact dermatitis, pollinosis, rheumatism, and inflammatory bowel disease, as well as can be used as cosmetics and foods or drinks, as described later.

Next, a method for producing the compounds Pa5, Pa5', and Pa9 according to the present disclosure will be described.

The method for producing the compounds Pa5, Pa5', and Pa9 according to the present disclosure comprises a step of performing extraction processing of a Lamiaceae plant.

Lamiaceae plants used may be plants of which the scientific names are *Perilla frutescens* (*Perilla frutesc-ens* Britton var. *crispa* and var. *acta* Kudo), and may also be allied species thereof (Labiatae). For example, green perilla, Ao-chirimen-jiso, red perilla, Chirimen-jiso, Katamen-jiso, and the like which are cultivated in Japan can be preferably used. Any Lamiaceae plant that exerts the effects of the present disclosure can be selected as appropriate. The available sites of the Lamiaceae plants, but are not particularly limited to, include entire plants, leaves, leafstalks, flowers, fruits, lateral roots, seeds, and the like. The sites may be used as is, the dried sites may be used, or the ground sites may be further used as extracts.

The extraction processing refers to subjection to common chemical separation and purification means such as extraction with a solvent, concentration, fractionation, or purification with a Lamiaceae plant as a raw material.

Examples of extraction methods include a method comprising extracting the ground product of a part or the whole of a plant by water or an organic solvent, ordinarily at 3 to 121° C. Examples of the organic solvent used in the extraction include, but are not particularly limited to: hydrocarbons such as petroleum ether, cyclohexane, toluene, and benzene; halogenated hydrocarbons such as carbon tetrachloride, dichloromethane, and chloroform; ethers; esters such as ethyl acetate; ketones such as acetone; alcohols such as methanol, ethanol, propanol, butanol, polyethylene glycol, propylene glycol, and butylene glycol; and pyridines. Such extracting solvents may be used singly, or in mixture of two or more kinds thereof. Preferably, a hydrous alcohol such as hydrous ethanol or hydrous methanol is used. From the viewpoint of the safety of the human body, examples of more preferred methods include a method comprising stirring and extracting the dried and ground product of a Lamiaceae plant using water amounting to 10 to 20 times the amount thereof or 60% ethanol amounting to 10 to 20 times the amount thereof at room temperature to 121° C. for 2 to 24 hours, and examples of still more preferred methods include hot water extraction (for example, heat reflux extraction for 30 minutes to 10 hours). An obtained extract may be used as is, or the obtained extract that is further subjected to processing such as concentration, filtration, or freeze drying as needed may be used. Such extracts and Lamiaceae plants may be used singly, or in combination of two or more kinds thereof. Any extraction method that exerts the effects of the present disclosure can be selected as appropriate.

A fractionation method for obtaining Pa5 and Pa5' will be exemplified below. A liquid solvent extract from a Lamiaceae plant is concentrated under reduced pressure, the obtained residue is suspended in water, and is subjected to partition extraction using ethyl acetate, and the liquid ethyl acetate extract is concentrated under reduced pressure. The obtained ethyl acetate-soluble part is subjected to silica gel column chromatography, and is eluted with a mixed solvent of n-hexane and acetone while sequentially increasing the ratio of the acetone. The fraction eluted with the mixed solvent of n-hexane:acetone=60:40 is re-subjected to silica gel column chromatography, and is eluted with a mixed solvent of chloroform and methanol while sequentially increasing the ratio of the methanol. The fraction eluted with the mixed solvent of chloroform:methanol=98:2 is subjected to preparatory thin layer chromatography, and is developed with a mixed solvent of chloroform:methanol=24:1. A moiety of Rf=0.82 is collected, and extracted with a mixed solvent of chloroform:methanol=1:1. The obtained liquid extract is concentrated under reduced pressure, is subjected to preparatory thin layer chromatography, and is developed with a mixed solvent of n-hexane:acetone=1:1. A moiety of Rf=0.44, which is collected for obtaining Pa5, and a moiety of Rf=0.70, which is collected for obtaining Pa5', are extracted with a mixed solvent of chloroform:methanol=1:1. Any method for fractionating Pa5 and Pa5' that exerts the effects of the present disclosure can be selected as appropriate.

A fractionation method for obtaining Pa9 will be exemplified below. A liquid solvent extract from a Lamiaceae plant is concentrated under reduced pressure, the obtained residue is suspended in water, and is subjected to partition extraction using ethyl acetate, and the liquid ethyl acetate extract is concentrated under reduced pressure. The obtained ethyl acetate-soluble part is subjected to silica gel column chromatography, and is eluted with a mixed solvent of n-hexane and acetone while sequentially increasing the ratio of the acetone. The fraction eluted with the mixed solvent of n-hexane:acetone=60:40 is re-subjected to silica gel column chromatography, and is eluted with a mixed solvent of chloroform and methanol while sequentially increasing the ratio of the methanol. The fraction eluted with the mixed solvent of chloroform:methanol=96:4 is subjected to column chromatography with octadecyl silica gel, and is eluted with a mixed solvent of water and methanol while sequentially increasing the ratio of the methanol. The fraction eluted with the mixed solvent of water:methanol=70:30 is subjected to preparatory thin layer chromatography, and is developed with a mixed solvent of chloroform:methanol=10:1. A moiety of Rf=0.70 is collected, and extracted with a mixed solvent of chloroform:methanol=1:1. Any method for fractionating Pa9 that exerts the effects of the present disclosure can be selected as appropriate.

Next, a medicine according to the present disclosure will be described.

The medicine according to the present disclosure comprises, as an active ingredient, the compound Pa5, Pa5', or Pa9 according to the present disclosure.

As the medicine according to the present disclosure, Pa5, Pa5', or Pa9 is used as is, or is used in combination with one or more pharmaceutically acceptable excipients or carriers. Further, the medicine according to the present disclosure may contain, as appropriate, a binder, a disintegrant, a thickener, a dispersant, a reabsorption promoter, a corrigent, a buffer, a surfactant, a solubilizer, a preservative, an emulsifier, an isotonizing agent, a stabilizer, a pH adjustor, and/or the like which are ordinarily used. Further, the medicine according to the present disclosure may contain another active ingredient as appropriate.

Examples of the dosage form of the medicine according to the present disclosure, depending on the kind and degree of a disease, and/or the like, include dosage forms suitable for oral, parenteral, or intranasal administration, tablets or sugar-coated tablets, sublingual tablets, gelatin capsules, lozenges, suppositories, creams, ointments, and skin gels.

The dose of the medicine according to the present disclosure differs depending on the age and body weight of a patient, the kind and seriousness of a disease, and the route of administration. For example, when orally administered to an adult, the medicine is administered at a dose of 0.1 to 500 mg, on the basis of Pa5, Pa5', or Pa9, once to three times daily.

Next, an anti-inflammatory agent according to the present disclosure will be described.

The anti-inflammatory agent according to the present disclosure comprises, as an active ingredient, the compound Pa5, Pa5', or Pa9 according to the present disclosure.

Pa5, Pa5', and Pa9 have excellent anti-inflammatory action as described in Examples later. Thus, Pa5, Pa5', and Pa9 can be used as anti-inflammatory agents in treatment of inflammatory diseases such as atopic dermatitis, contact dermatitis, pollinosis, rheumatism, and inflammatory bowel disease.

The dosage form, dose, and the like of the anti-inflammatory agent according to the present disclosure are as described above.

Next, a cosmetic and a food or drink according to the present disclosure will be described.

The cosmetic and the food or drink according to the present disclosure comprise the compound Pa5, Pa5', or Pa9 according to the present disclosure.

In the cosmetic according to the present disclosure, Pa5, Pa5', or Pa9 as well as the dry powder or extract of the Lamiaceae plant described above can be added to a skin care product, a foundation, a makeup product, or the like for the purpose of alleviating or preventing the symptoms of atopic dermatitis and contact dermatitis.

The food or drink according to the present disclosure is used for the purpose of alleviating or preventing the symptoms of atopic dermatitis, contact dermatitis, pollinosis, and the like, and Pa5, Pa5' or Pa9 can be blended into a common food, a supplement, a specified health food, a special nutritious food, a nutritional supplementary food, a health food, or the like in order to sufficiently exert the function of the food. Not only Pa5, Pa5', or Pa9 is added but also the dry powder or extract of the Lamiaceae plant described above can be used. It is possible to add the dry powder or the extract to various foods. Examples of the drink include drinks as specified health foods, special nutritious foods, and nutritional supplementary foods, as well as other nutritious drinks, health drinks, and various health teas. Examples of other foods include confectionery, breads, noodles, fish-paste products, oils and fats, and seasonings.

The amount of Pa5, Pa5' or Pa9 blended into the cosmetic and the food or drink according to the present disclosure is not particularly limited but is commonly 0.001 to 100% by weight, and particularly preferably 0.01 to 50% by weight, in terms of dry solid content.

EXAMPLES

The present disclosure will be specifically described below with reference to examples. However, the present disclosure is not limited to the examples.

Example 1

From perilla leaves, 8-hydroxy-6,7-dimethoxyflavanone (Pa5) was extracted and purified.

(Extraction with Methanol)

Reflux extraction with 44.3 L of methanol was performed twice (for 1 hour) using 4.40 kg of green perilla (*Perilla frutescens* f. *viridis*) leaves. The liquid methanol extracts obtained by performing the reflux extraction twice were concentrated under reduced pressure to obtain 772 g of methanol extract (17.5%). In 3.9 L of water, 772 g of the methanol extract was suspended, and the resultant was subjected to partition extraction three times using 3.9 L of ethyl acetate. The liquid ethyl acetate extracts obtained by performing the partition extraction three times were combined and concentrated under reduced pressure to obtain 254.7 g of ethyl acetate-soluble part.

To silica gel column chromatography (7.5 cm i.d.×49 cm), 87.7 g of the obtained ethyl acetate-soluble part was subjected, and the resultant was eluted with a mixed solvent of n-hexane and acetone while sequentially increasing the ratio of the acetone. To silica gel column chromatography (3.0 cm i.d.×25 cm), 4.24 g of the fraction eluted with the mixed solvent of n-hexane:acetone=60:40 was re-subjected, and the resultant was eluted with a mixed solvent of chloroform and methanol while sequentially increasing the ratio of the methanol. To preparatory thin layer chromatography (silica gel 70, Wako Pure Chemical Industries, Ltd.), 383.2 mg of the fraction eluted with the mixed solvent of chloroform:methanol=98:2 was subjected, and the resultant was developed with a mixed solvent of chloroform:methanol=24:1. A moiety of Rf=0.82 was collected, and extracted with a mixed solvent of chloroform:methanol=1:1. The obtained liquid extract was concentrated under reduced pressure to obtain 195.7 mg of light brown residue. The light brown residue was re-subjected to preparatory thin layer chromatography (silica gel 70, Wako Pure Chemical Industries, Ltd.), and was developed with a mixed solvent of n-hexane:acetone=1:1. A moiety of Rf=0.44 was extracted with a mixed solvent of chloroform:methanol=1:1. The liquid extract was concentrated under reduced pressure, and the obtained white powder was crystallized with a mixed solvent of chloroform and methanol to obtain 82.3 mg of colorless prism crystals.

The analytical data of the colorless prism crystals obtained as described above will be described below:

mp 166-168° C.

$[\alpha]^{23}_D 0$ (c1.03, MeOH)

IR v (KBr) cm$^{-1}$: 3290 (OH), 1672 (C=O), 1605 (aromatic ring)

UV $\lambda_{max}$ (MeOH) nm (c): 201 (27074), 244 (11253), 288 (13489), 349 (5085)

ESI-MS m/z: 301 [M+H]$^+$, 197

Positive HR-ESI-MS m/z 301.1068 [M+H]$^+$, Calcd for $C_{17}H_{17}O_5$: 301.1076.

CD (c=0.00114, MeOH) $\Delta\epsilon$ (nm): 0 (220-400)

$^1$H-NMR δ in CDCl$_3$: 2.85 (1H, dd, J=16.5, 2.8 Hz), 3.08 (1H, dd, J=16.5, 12.8 Hz), 3.92 (3H, s, OCH$_3$), 4.02 (3H, s, OCH$_3$), 5.03 (1H, s, disappeared with D$_2$O), 5.46 (1H, dd, J=12.8, 2.8 Hz), 6.19 (1H, s, H-5), 7.41-7.49 (5H, m).

$^{13}$C-NMR δ in CDCl$_3$: 45.8 (C-3), 56.2 (OCH$_3$), 56.3 (OCH$_3$), 80.0 (C-2), 89.6 (C-5), 105.7 (C-4a), 126.3 (C-2', C-5'), 127.6 (C-8a), 128.85 (C-3', C-5'), 128.89 (C-4'), 138.3 (C-1'), 149.4 (C-8), 152.5 (C-7), 155.0 (C-6), 189.4 (C-4).

Based on the above, it was found that the colorless prism crystals obtained as described above contained 8-hydroxy-6,7-dimethoxyflavanone (Pa5).

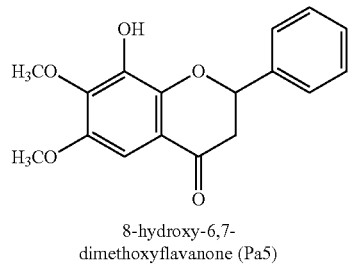 [SMILES: COc1cc2c(c(O)c1OC)OC(c1ccccc1)CC2=O]

8-hydroxy-6,7-
dimethoxyflavanone (Pa5)

(Extraction with Hot Water)

Heat reflux extraction of 0.6 kg of green perilla (*Perilla frutescens* f. *viridis*) leaves was performed (for 1 hour) with 1 L of water. The resultant was cooled, followed by filtering the liquid extract through filter paper (Advantec Qualitative Filter Paper No. 2). Partition extraction of 9.5 L of the hot-water extract obtained in such a manner was performed three times using 9.5 L of ethyl acetate. The liquid ethyl acetate extracts obtained by performing the partition extraction three times were combined and concentrated under reduced pressure to obtain 8.78 g of ethyl acetate-soluble part.

To silica gel column chromatography (3.0 cm i.d.×30 cm), 8.78 g of the obtained ethyl acetate-soluble part was subjected, and the resultant was eluted with a mixed solvent of n-hexane and acetone while sequentially increasing the ratio of the acetone. To silica gel column chromatography (3.0 cm i.d.×25 cm), 0.425 g of the fraction eluted with the mixed solvent of n-hexane:acetone=60:40 was re-subjected, and the resultant was eluted with a mixed solvent of chloroform and methanol while sequentially increasing the ratio of the methanol. To preparatory thin layer chromatography (silica gel 70, Wako Pure Chemical Industries, Ltd.), 39.1 mg of the fraction eluted with the mixed solvent of chloroform:methanol=98:2 was subjected, and the resultant was developed with a mixed solvent of chloroform:methanol=24:1. A moiety of Rf=0.82 was collected, and extracted with a mixed solvent of chloroform:methanol=1:1. The obtained liquid extract was concentrated under reduced pressure to obtain 20.5 mg of light brown residue. The light brown residue was re-subjected to preparatory thin layer chromatography (silica gel 70, Wako Pure Chemical Industries, Ltd.), and was developed with a mixed solvent of n-hexane:acetone=1:1. A moiety of Rf=0.44 was extracted with a mixed solvent of chloroform:methanol=1:1. The liquid extract was concentrated under reduced pressure, and the obtained white powder was crystallized with a mixed solvent of chloroform and methanol to obtain 9.1 mg of colorless prism crystals. As a result of analysis, it was found that the colorless prism crystals contained 8-hydroxy-6,7-dimethoxyflavanone (Pa5) similarly as described above.

Example 2

From perilla leaves, 5,8-dihydroxy-7-methoxyflavanone (Pa5') was extracted and purified.

(Extraction with Methanol)

Reflux extraction with 44.3 L of methanol was performed twice (for 1 hour) using 4.40 kg of green perilla (*Perilla frutescens* f. *viridis*) leaves. The liquid methanol extracts obtained by performing the reflux extraction twice were concentrated under reduced pressure to obtain 772 g of methanol extract (17.5%). In 3.9 L of water, 772 g of the methanol extract was suspended, and the resultant was subjected to partition extraction three times using 3.9 L of ethyl acetate. The liquid ethyl acetate extracts obtained by performing the partition extraction three times were combined and concentrated under reduced pressure to obtain 254.7 g of ethyl acetate-soluble part.

To silica gel column chromatography (7.5 cm i.d.×49 cm), 87.7 g of the obtained ethyl acetate-soluble part was subjected, and the resultant was eluted with a mixed solvent of n-hexane and acetone while sequentially increasing the ratio of the acetone. To silica gel column chromatography (3.0 cm i.d.×25 cm), 4.24 g of the fraction eluted with the mixed solvent of n-hexane:acetone=60:40 was re-subjected, and the resultant was eluted with a mixed solvent of chloroform and methanol while sequentially increasing the ratio of the methanol. To preparatory thin layer chromatography (silica gel 70, Wako Pure Chemical Industries, Ltd.), 383.2 mg of the fraction eluted with the mixed solvent of chloroform:methanol=98:2 was subjected, and the resultant was developed with a mixed solvent of chloroform:methanol=24:1. A moiety of Rf=0.82 was collected, and extracted with a mixed solvent of chloroform:methanol=1:1. The obtained liquid extract was concentrated under reduced pressure to obtain 195.7 mg of light brown residue. The light brown residue was re-subjected to preparatory thin layer chromatography (silica gel 70, Wako Pure Chemical Industries, Ltd.), and was developed with a mixed solvent of n-hexane:acetone=1:1. A moiety of Rf=0.70 was extracted with a mixed solvent of chloroform:methanol=1:1. The liquid extract was concentrated under reduced pressure, and the obtained yellow powder was crystallized from methanol to obtain 14.4 mg of crystalline powder (yield of 0.00095%).

The analytical data of the crystalline powder obtained as described above will be described below:

Yellow needles (from MeOH). mp 220-225° C.

UV $\lambda_{max}$ (MeOH) nm (log ε): 246 (3.97), 292 (4.16), 364 (3.62) nm.

$[\alpha]^{23}_D$0 (c0.253, MeOH) CD (c=0.00172, MeOH) Δε (nm): 0 (220-400)

Positive MALDI-TOF-MS (matrix: adipic acid.): m/z (%): 287.30 ([M+H]$^+$, 100), 288.30 (17), 289.31 (3).

$^1$H-NMR (DMSO-$d_6$) δ2.78 (1H, dd, J=16.9, 3.2 Hz), and 3.19 (1H, dd, J=16.9, 12.4 Hz) (H-3), 3.77 (3H, s, OCH$_3$), 5.51 (1H, dd, J=12.4, 3.2 Hz, H-2), 6.15 (1H, s, H-7), 7.35 (2H, m, H-3', -5'), 7.36 (1H, m, H-4'), 7.48 (2H, m, H-2', -6'), 8.15 (1H, s, OH), 11.74 (1H, s, OH).

$^{13}$C-NMR (DMSO-$d_6$) δ42.7 (C-3). 56.4 (OCH$_3$), 78.6 (C-2), 92.8 (C-6), 102.6 (C-4), 126.9 (C-2', 6'), 128.66 (C-3', -5', 128.72 (C-4'), 139.1 (C-1'), 148.3 (C-8a), 156.0 (C-5), 157.5 (C-8), 197.2 (C-4).

Based on the above, it was found that the crystalline powder obtained as described above contained 8-dihydroxy-7-methoxyflavanone (Pa5').

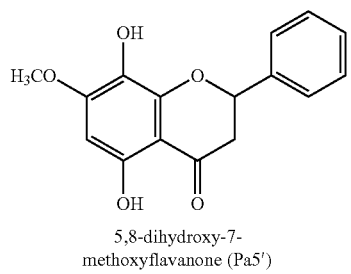 [SMILES: COc1cc(O)c2c(c1O)OC(c1ccccc1)CC2=O]

5,8-dihydroxy-7-methoxyflavanone (Pa5')

(Extraction with Hot Water)

Heat reflux extraction of 0.6 kg of green *perilla* (*Perilla frutescens* f. *viridis*) leaves was performed (for 1 hour) with 1 L of water. The resultant was cooled, followed by filtering the liquid extract through filter paper (Advantec Qualitative Filter Paper No. 2). Partition extraction of 9.5 L of the hot-water extract obtained in such a manner was performed three times using 9.5 L of ethyl acetate. The liquid ethyl acetate extracts obtained by performing the partition extraction three times were combined and concentrated under reduced pressure to obtain 8.78 g of ethyl acetate-soluble part.

To silica gel column chromatography (3.0 cm i.d.×30 cm), 8.78 g of the obtained ethyl acetate-soluble part was subjected, and the resultant was eluted with a mixed solvent of n-hexane and acetone while sequentially increasing the ratio of the acetone. To silica gel column chromatography (3.0 cm i.d.×25 cm), 0.425 g of the fraction eluted with the mixed solvent of n-hexane:acetone=60:40 was re-subjected, and the resultant was eluted with a mixed solvent of chloroform and methanol while sequentially increasing the ratio of the methanol. To preparatory thin layer chromatography (silica gel 70, Wako Pure Chemical Industries, Ltd.), 39.1 mg of the fraction eluted with the mixed solvent of chloroform:methanol=98:2 was subjected, and the resultant was developed with a mixed solvent of chloroform:methanol=24:1. A moiety of Rf=0.82 was collected, and extracted with a mixed solvent of chloroform:methanol=1:1. The obtained liquid extract was concentrated under reduced pressure to obtain 20.5 mg of light brown residue. The light brown residue was re-subjected to preparatory thin layer chromatography (silica gel 70, Wako Pure Chemical Industries, Ltd.), and was developed with a mixed solvent of n-hexane:acetone=1:1. A moiety of Rf=0.70 was extracted with a mixed solvent of chloroform:methanol=1:1. The liquid extract was concentrated under reduced pressure, and the obtained yellow powder was crystallized from methanol to obtain 2.0 mg of crystalline powder. As a result of analysis, it was found that the crystalline powder contained 8-dihydroxy-7-methoxyflavanone (Pa5') similarly as described above.

Example 3

From perilla leaves, esculetin (Pa9) was extracted and purified.

(Extraction with Methanol)

Reflux extraction with 44.3 L of methanol was performed twice (for 1 hour) using 4.40 kg of green perilla (*Perilla frutescens* f. *viridis*) leaves. The liquid methanol extracts obtained by performing the reflux extraction twice were concentrated under reduced pressure to obtain 772 g of methanol extract (17.5%). In 3.9 L of water, 772 g of the methanol extract was suspended, and the resultant was subjected to partition extraction three times using 3.9 L of ethyl acetate. The liquid ethyl acetate extracts obtained by performing the partition extraction three times were combined and concentrated under reduced pressure to obtain 254.7 g of ethyl acetate-soluble part.

To silica gel column chromatography (7.5 cm i.d.×49 cm), 87.7 g of the obtained ethyl acetate-soluble part was subjected, and the resultant was eluted with a mixed solvent of n-hexane and acetone while sequentially increasing the ratio of the acetone. To silica gel column chromatography (3.0 cm i.d.×25 cm), 4.24 g of the fraction eluted with the mixed solvent of n-hexane:acetone=60:40 was re-subjected, and the resultant was eluted with a mixed solvent of chloroform and methanol while sequentially increasing the ratio of the methanol. To octadecyl silica gel column chromatography, 1167 mg of the fraction eluted with the mixed solvent of chloroform:methanol=96:4 was subjected, and the resultant was eluted with a mixed solvent of water and methanol while sequentially increasing the ratio of the methanol. To preparatory thin layer chromatography (silica gel 70, Wako Pure Chemical Industries, Ltd.), 82 mg of the fraction eluted with the mixed solvent of water:methanol=70:30 was subjected, and the resultant was developed with a mixed solvent of chloroform:methanol=10:1. A moiety of Rf=0.70 was collected, and extracted with a mixed solvent of chloroform:methanol=1:1. The liquid extract was concentrated under reduced pressure, and the obtained residue was crystallized with methanol to obtain 9.7 mg of light brown needle crystals.

The analytical data of the light brown needle crystals obtained as described above will be described below:

mp 255-258° C.

UV $\lambda_{max}$ (MeOH) nm (log ε): 228 (4.00), 259 (3.61), 299 (3.65), 347 (3.81)

Negative MALDI-TOF-MS m/z (%): 177.24 ([M−H]⁻, 100), 178.24 (15).

$^1$H-NMR δ in MeOH-d$_4$: 6.17 (1H, d, J=9.6 Hz), 6.75 (1H, s), 6.93 (1H, s), 7.78 (1H, d, J=9.6 Hz).

Based on the above, it was found that the light brown needle crystals obtained as described above contained esculetin (Pa9).

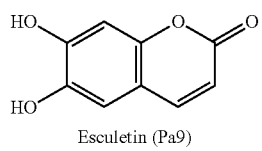

Esculetin (Pa9)

(Extraction with Hot Water)

Heat reflux extraction of 0.66 kg of green perilla (*Perilla frutescens* f. *viridis*) leaves was performed (for 1 hour) with 11 L of water. The resultant was cooled, followed by filtering the liquid extract through filter paper (Advantec Qualitative Filter Paper No. 2). Partition extraction of 9.5 L of the hot-water extract obtained in such a manner was performed three times using 9.5 L of ethyl acetate. The liquid ethyl acetate extracts obtained by performing the partition extraction three times were combined and concentrated under reduced pressure to obtain 8.78 g of ethyl acetate-soluble part.

To silica gel column chromatography (3.0 cm i.d.×30 cm), 8.78 g of the obtained ethyl acetate-soluble part was subjected, and the resultant was eluted with a mixed solvent of n-hexane and acetone while sequentially increasing the ratio of the acetone. To silica gel column chromatography (3.0 cm i.d.×25 cm), 0.425 g of the fraction eluted with the mixed solvent of n-hexane:acetone=60:40 was re-subjected, and the resultant was eluted with a mixed solvent of chloroform and methanol while sequentially increasing the ratio of the methanol. To octadecyl silica gel column chromatography, 117.7 mg of the fraction eluted with the mixed solvent of chloroform:methanol=96:4 was subjected, and the resultant was eluted with a mixed solvent of water and methanol while sequentially increasing the ratio of the methanol. To preparatory thin layer chromatography (silica gel 70, Wako Pure Chemical Industries, Ltd.), 9.5 mg of the fraction eluted with water:methanol=70:30 was subjected, and the resultant was developed with a mixed solvent of chloroform: methanol=10:1. A moiety of Rf=0.70 was collected, and extracted with a mixed solvent of chloroform:methanol=1:1. The liquid extract was concentrated under reduced pressure, and the obtained residue was crystallized with methanol to obtain 1.1 mg of light brown needle crystals. As a result of analysis, it was found that the crystalline powder contained esculetin (Pa9) similarly as described above.

Example 4

The action of inhibiting production of nitrogen monoxide (NO) was examined to investigate the anti-inflammatory action of Pa5.

Nitrogen monoxide (NO) is known as one of inflammation mediators induced by interleukin (IL)-1β, and NO production inhibitory action can be regarded as an index of anti-inflammatory action. In the present example, it was investigated whether or not Pa5 has anti-inflammatory action by examining the NO production inhibitory action of Pa5. Negletein reported to exist in green perilla and to have NO production inhibitory action was used as a comparative example.

Liver cells were isolated from male Wistar rats (200 to 250 g, Charles River) by a collagenase perfusion method (collagenase: Wako Pure Chemicals). The isolated liver cells were suspended in a medium at 6×10⁵ cells/mL, seeded in 35 mm plastic dishes (Falcon Plastic) (2 mL/dish), and cultured in an incubator with 5% $CO_2$ at 37° C. Williams' Medium E (WE) containing 10% newborn calf serum, HEPES (5 mM), penicillin (100 U/mL), streptomycin (0.1 mg/mL), dexamethasone (10 nM), and insulin (10 nM) was used as the medium. After 5 hours, the medium was replaced with fresh WE free of any serum and hormone, and the cells were cultured overnight until before use of the cells for an experiment.

On day 1 after the start of the culture, cells were subjected to replacement with fresh WE free of any serum and hormone, and recombinant rat IL-1β (purity of 97% or more) (PeproTech, Rocky Hill, N.J., USA), and Pa5 extracted with methanol in Example 1 or negletein in the comparative example were added to the medium. In each medium, the concentration of IL-1β was 1 nM, the concentrations of Pa5 were 5, 10, and 20 μM, and the concentrations of negletein were 10, 20, and 40 μM (FIG. 1). The amount of NO in each medium was measured 8 hours after the addition of IL-1β, and Pa5 or negletein by a Griess method (Green L C et al, Anal Biochem 1982; 126: 131-138). More specifically, the amount of nitrite (stable metabolite of NO) in each medium was measured.

Further, lactate dehydrogenase (LDH) activity was measured to investigate the cytotoxicity of Pa5. The lactate dehydrogenase (LDH) activity of each medium was measured using LDH Cytotoxicity Detection Kits (Takara Bio Inc.). LDH is an enzyme existing in a cell, and therefore migrates into a medium due to cell damage. Each medium was collected 8 hours after the addition of IL-1β, and Pa5 or negletein, and was used for measuring the activity. Actually, each sample (50 μl of medium) and Solution C (50 μl) in the kit were mixed and left standing at room temperature for 30 minutes, 1 M hydrochloric acid (25 μl) was added to stop the reaction, and the absorbance of the resultant at 490 nm was measured and compared with a calibration curve using LDH of known concentration to determine the LDH activity. The LDH activity of the whole cells on one dish (that is, whole-cell extract) was considered to be a positive control (positive control in FIG. 3), and was regarded as 100%. The medium was removed from each dish containing the liver cells, the cells were washed three times with phosphate buffered saline (PBS), then ultrasonically broken, and centrifuged at 10000×g for 3 minutes to then obtain a supernatant, which was used as a whole-cell extract, and the LDH activity of the cells was measured.

Figure 2:
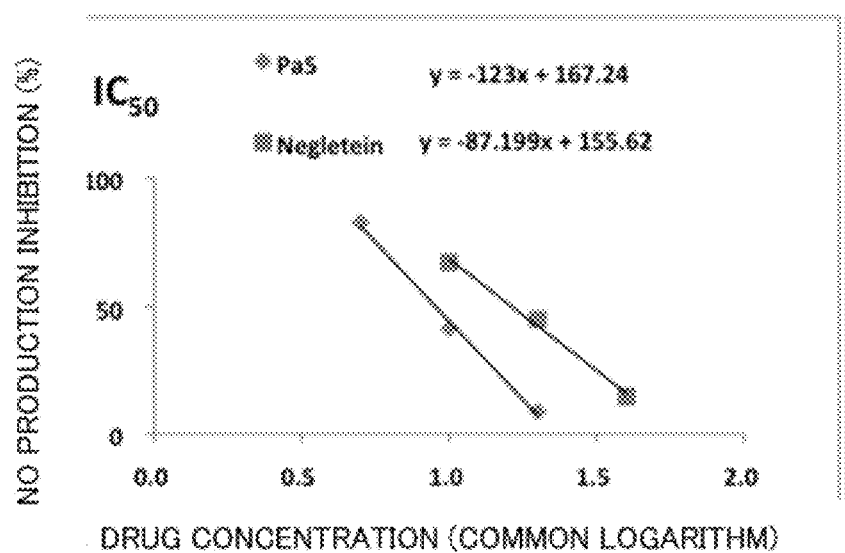
FIG. 2 is a view showing the results of measurement of $IC_{50}$ values.

The results of the measurement of NO productions in the rat liver cells are shown in FIG. 1, and IC$_{50}$ values (drug concentrations at NO production of 50%) are shown in FIG. 2. In FIG. 1, "(−)" means no addition of IL-1β while "(+)" means addition of IL-1β. Although both Pa5 and negletein (comparative example) dose-dependently inhibited the production of NO due to IL-1β, the degree of the NO production inhibitory action of Pa5 was higher than that of negletein (comparative example) in comparison between Pa5 and negletein (comparative example) at the same addition concentration (10 μM) (FIG. 1). Further, the IC$_{50}$ value of Pa5 was 9.0 µM whereas the $IC_{50}$ value of negletein (comparative example) was 16.3 µM (FIG. 2), and it was thus shown that the NO production inhibitory action of Pa5 was higher than that of negletein (comparative example).

Figure 3:
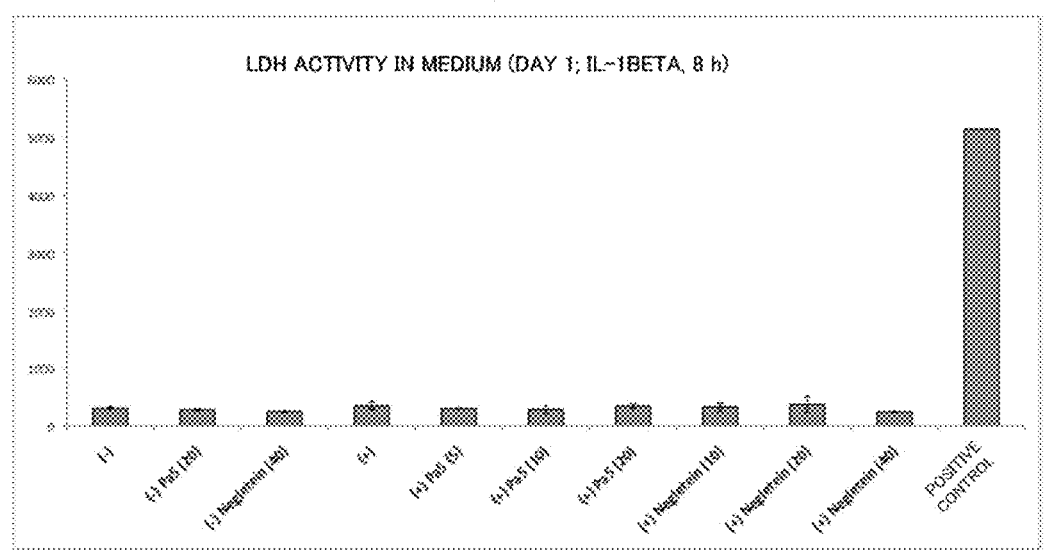
FIG. 3 is a view showing the results of measurement of LDH activity.

The results of measurement of LDH activity are shown in FIG. 3. In FIG. 3, "(−)" means no addition of IL-1β while "(+)" means addition of IL-1β. The LDH activity in the case of adding Pa5 was equivalent to that in the case of adding IL-1β, and it was thus suggested that Pa5 had no cytotoxicity.

Based on the above, it was shown that Pa5 has high NO production inhibitory action. Thus, it was revealed that Pa5 has excellent anti-inflammatory action.

Example 5

The influences of Pa5 and Pa5' on the production of various inflammatory cytokines/chemokines were investigated by cytokine/chemokine arrays (in vitro).

In the early stage of inflammation, several kinds of chemotactic factors are released from a damaged tissue, and leukocytes infiltrate into the inflammatory site. Chemotactic factors include factors having low specificities, such as leukotriene B4 (LTB4), and members of the chemokine family, which are proteinaceous chemotactic factors having high specificities. Chemokines are broadly classified into two kinds of CXC chemokine in which one residue is present between the two Cys residues ahead in four contained Cys residues and of CC chemokine in which the Cys residues continues. The former generally has neutrophil chemotactic activity, and the latter has monocyte chemotactic activity. It has been revealed that specific chemokines are excessively expressed in inflammatory diseases. It is expected that an anti-inflammatory drug can be targeted for controlling the signaling of a chemokine and a receptor therefor.

In the present example, the influences of Pa5 and Pa5' on the production of the various inflammatory cytokines/chemokines due to the addition of IL-1β were investigated by the cytokine/chemokine arrays (in vitro).

In like manner with Example 4, liver cells were isolated from male Wistar rats by a collagenase perfusion method. The isolated liver cells were suspended in a medium (similar to that in Example 4) at $1.2 \times 10^6$ cells/mL, seeded in 35 mm plastic dishes (similar to those in Example 4) (1 mL/dish), and cultured in an incubator with 5% $CO_2$ at 37° C. After 5 hours, the medium was replaced with fresh WE free of any serum and hormone, and the cells were cultured overnight until before use of the cells for an experiment.

On day 1 after the start of the culture, cells were subjected to replacement with fresh WE free of any serum and hormone, and IL-1β (similar to that in Example 4), and Pa5 extracted with methanol in Example 1 or Pa5' extracted with methanol in Example 2 were added to the medium. The concentrations of IL-1β, Pa5, and Pa5' in each medium were 1 nM, 20 µM, and 100 µM, respectively (Table 1). Then, the cells were cultured at 37° C., and the medium was collected 3 hours after the start of the culture. The collected medium was centrifuged for 1 minute at 5000 rpm to remove cellular debris, and the supernatant was used in an assay. The supernatant was preserved at −80° C. until performing the assay.

The productions of the various inflammatory cytokines/chemokines were measured according to an accompanying protocol using Rat Cytokine Antibody Array (R&D Systems) (http://www.rndsystems.com/product_detail_object-name_ratcytokinearray.aspx) capable of detecting 29 kinds of cytokines/chemokines in Proteome Profiler® Antibody Array. In the measurement, 1 mL of the supernatant of the medium obtained as described above was used.

In the above-described method, the 29 kinds of the cytokines/chemokines can be detected at once, and chemiluminescence on the filter of Proteome Profiler Antibody Array increases in proportion to the amount of each cytokine/chemokine. Thus, the chemiluminescence on the filter of Proteome Profiler Antibody Array was detected with LAS3000mini (GE Healthcare), subjected to densitometry analysis, and converted into a numeric value. The densitometry analysis was carried out with reference to http://www.hm6.aitai.ne.jp/~maxcat/imageJ/technique.html#gels (the heading of "Analyzing Electrophoretic Gels") using ImageJ software.

The details of the various inflammatory cytokines/chemokines are described below.

(1) CINC-2α/β and (2) CINC-3

Cytokine-induced neutrophil chemoattractants (CINCs) belong to the alpha (CXC) subfamily of chemokines. Three rat CXC chemokines (CINC-2α, CINC-2β, and CINC-3/MIP-2) as well as CINC-1 have been identified. Neutrophil infiltration is a typical acute-phase inflammatory reaction, and results in immediate morphological change of neutrophils in response to the stimuli of CINCs. Examination performed in vitro shows no substantial differences between the chemotactic activities of the respective CINCs, while examination performed in vivo shows strong chemotactic activities specific for neutrophils. The inhibition of the expression of CINCs results in the inhibition of neutrophil infiltration in local inflammation, and is expected to result in the alleviation of inflammatory symptoms.

(3) Fractalkine (CX3CL1)

Fractalkine (CX3CL1) is expressed in activated vascular endothelial cells, nerve cells, dendritic cells, and intestinal epithelial cells. The expression of CX3CL1 is induced by the inflammatory stimuli of TNFα, IL-1, IFNγ, and the like which are inflammatory cytokines. CX3CL1 is present in two membrane-bound and secreted forms in vivo, and functions not only as a chemokine but also as a cell adhesion molecule exhibiting cell adhesion in an integrin-independent manner. The secreted chemokine exhibits chemotaxis activity for NK cells, T cells, and monocytes. CX3CL1 also has angiogenic action. The expression of fractalkine-CX3CR1 is known to be involved in various diseases such as rheumatoid arthritis and arteriosclerosis. The inhibition of CX3CL1 can result in the inhibition of inflammatory cell infiltration into a synovial tissue, and is expected to result in the inhibition of inflammations including arthritis such as rheumatoid arthritis.

(4) sICAM-1 (CD54)

CD54 (intercellular adhesion molecule 1 (ICAM-1)), which is an adhesion molecule, transmembrane glycoprotein, belonging to the immunoglobulin superfamily, is constantly expressed in many cells. CD54 is bound to a cell adhesion molecule, lymphocyte function-associated antigen 1 (LFA-1), and plays important roles in cell-to-cell interactions in inflammation and immune responses. Soluble intercellular adhesion molecule (sICAM) among ICAMs controls an immune reaction through ICAM and is known to be increasingly expressed due to autoimmune diseases, endocrine diseases, gastric cancer, pancreatic cancer, breast cancer, and the like. The increased expression is considered to result in the inhibition of cytotoxic T cells and natural killer cells from attacking cancer cells, and in the promotion of cancer metastasis.

(5) MIG (CXCL9)

CXCL9, which is a 14 kDa chemokine, is a member of the CXC chemokine family. CXCL9 is specifically induced in macrophages, monocytes, neutrophils, APCs, B cells, and eosinophils, and the mechanism of the induction is made through an IFNγ-JAK/STAT signaling pathway. Thus, CXCL9 is also referred to as a monokine induced by gamma interferon (MIG). In vein endothelial cells and skin fibroblasts, the induction of CXCL9 is promoted by TNFα. CXCL9 is also constitutively expressed in the intestinal epithelium. The major function of the chemokine is the recruitment of leukocytes into infection and inflammation sites, and several studies have reported that CXCL9 is activated due to infections with Gram-negative or Gram-positive bacteria. CXCL9 is closely involved in immune responses in rheumatoid arthritis and the like, and chronic inflammations. The expression of CXCL9 is also considered to be likely to function as a mediator for the recruitment and activation of T cells in psoriasis and lung diseases. CXCL9 is also expressed prior to rejection, several days after dermal graft.

(6) VEGF (VEGF-A/Vasculotropin)

Vascular endothelial growth factor (VEGF), which is one of factors involved in vascularization, plays an important role in growth of solid cancers. VEGF-A has two properties of a growth factor for vascular endothelial cell and a vascular permeability enhancement factor. The gene expression of VEGF-A is induced by a growth factor, estrogen, hypoxia, and/or the like. Based on the fact that, for example, an antibody medicine, bevacizumab, which is specifically bound to VEGF and inhibits the function of VEGF, shows an excellent survival advantage, it has been demonstrated that the inhibition of VEGF is proper for the strategy of treatment of a solid cancer. Furthermore, involvement of a VEGF system has been shown in a mouse model of rheumatoid arthritis, an arteriosclerosis model, or the like. VEGFR is considered to be deeply involved in inflammation through the mobilization and function activation of inflammatory cells, and it can be considered that suppression of the expression of VEGFR leads to anti-inflammatory action.

(7) IL-17

IL-17 (IL-17A) is a cytokine identified as CTLA-8 from a cDNA library from activated murine T cells. The induction of the expression of cytokines/chemokines, such as IL-6, G-CSF, CXCL1, and CXCL8 (only human), generally involved in the activation and migration of neutrophils, and antimicrobial peptides such as β-defensin and the S100 family is known as the action of IL-17. Since autoimmune diseases such as collagen-induced arthritis and autoimmune encephalomyelitis were worsened rather than inhibited in IFN-γ- and IL-12-deficient mice whereas the autoimmune diseases were strongly inhibited in IL-17-deficient mice, and human clinical trials using anti-IL-17 antibodies showed the efficacy of the anti-IL-17 antibodies for rheumatoid arthritis and psoriasis, it is suggested that the inhibition of the expression of IL-17 is effective for improving inflammatory diseases.

(8) Thymus Chemokine (CXCL7)

CXCL7, which is generally produced from platelets due to activation, promotes the migration of neutrophils, basophils, fibroblasts, and monocytes, as well as the growth of fibroblasts, and the secretion of hyaluronic acid, glycosaminoglycan, PGE2, and the like. CXCL7 also promotes histamine release from basophils. The inhibition of the expression of CXCL7 results in the inhibition of the infiltration of neutrophils and the like and in the prevention of the promotion of histamine release, and is therefore suggested to act on anti-inflammatory properties.

Figure 4:
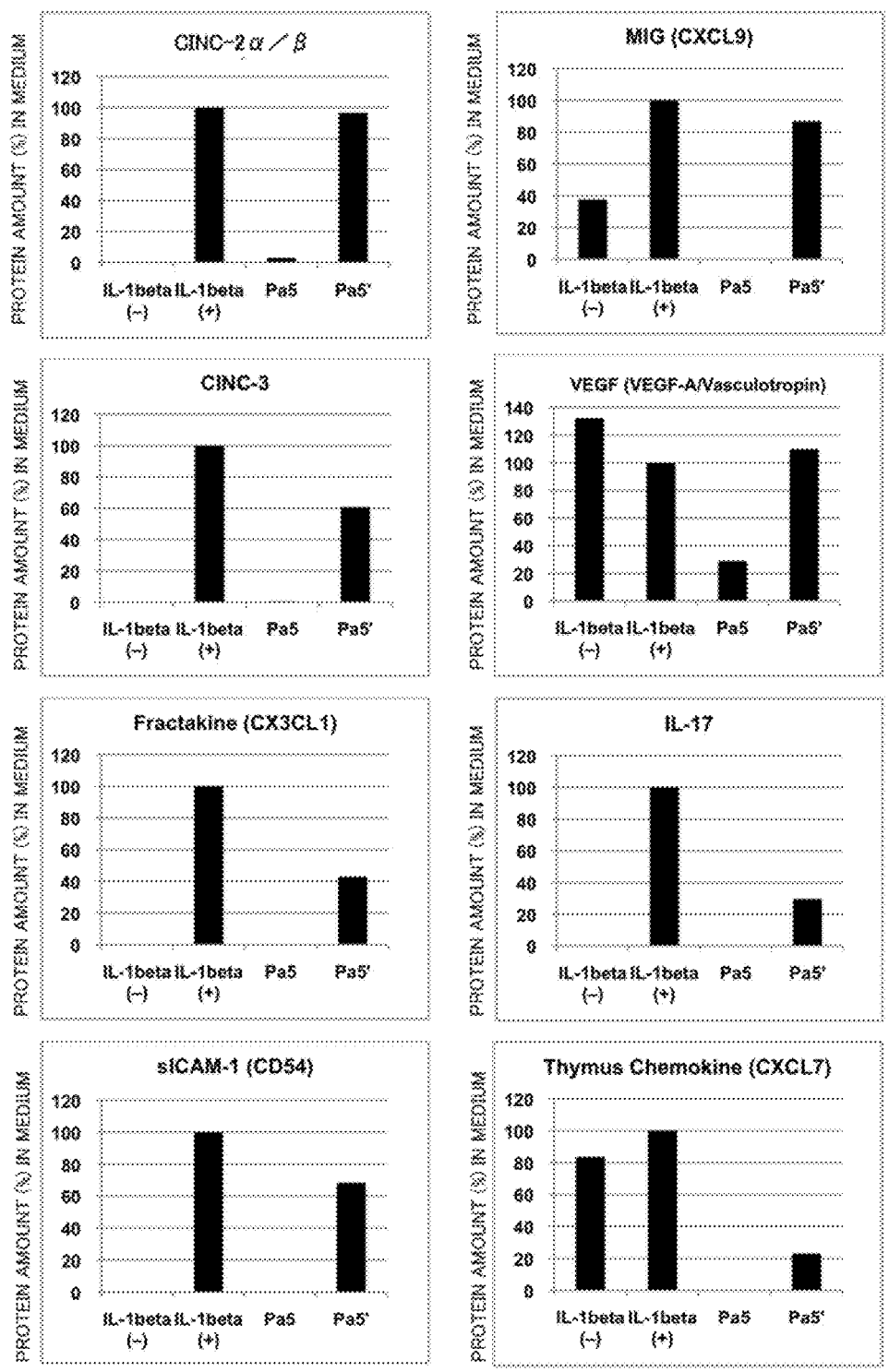
FIG. 4 is a view showing the results of cytokine/chemokine arrays (in vitro)

The results of the cytokine/chemokine arrays (in vitro) are shown in Table 1 and FIG. 4. In Table 1 and FIG. 4, "(−)" means no addition of IL-1β while "(+)" means addition of IL-1β. Pa5 was shown to strongly inhibit the induction of various cytokines/chemokines. Pa5' was also shown to strongly inhibit the induction of fractalkine (CX3CL1), IL-17, and thymus chemokine (CXCL7).

TABLE 1

| No. | | | | Average | (%) |
|---|---|---|---|---|---|
| (1) CINC-2α/β | | | | | |
| 1 | (−) | 0.0 | 0.0 | 0.0 | 0.0 |
| 2 | (+) | 5893.9 | 6176.6 | 6035.2 | 100.0 |
| 3 | (+) Pa5 (20 μM) | 209.7 | 130.6 | 170.2 | 2.8 |
| 4 | (+) Pa5' (100 μM) | 5944.2 | 5735.0 | 5839.6 | 96.8 |
| (2) CINC-3 | | | | | |
| 1 | (−) | 0.0 | 0.0 | 0.0 | 0.0 |
| 2 | (+) | 3044.9 | 3030.7 | 3037.8 | 100.0 |
| 3 | (+) Pa5 (20 μM) | 16.1 | 18.1 | 17.1 | 0.6 |
| 4 | (+) Pa5' (100 μM) | 1849.2 | 1844.7 | 1846.9 | 60.8 |
| (3) Fractakine (CX3CL1) | | | | | |
| 1 | (−) | 0.0 | 0.0 | 0.0 | 0.0 |
| 2 | (+) | 732.1 | 719.8 | 725.9 | 100.0 |
| 3 | (+) Pa5 (20 μM) | 0.0 | 0.0 | 0.0 | 0.0 |
| 4 | (+) Pa5' (100 μM) | 287.0 | 333.3 | 310.1 | 42.7 |
| (4) sICAM-1 (CD54) | | | | | |
| 1 | (−) | 0.0 | 0.0 | 0.0 | 0.0 |
| 2 | (+) | 413.0 | 339.4 | 376.2 | 100.0 |
| 3 | (+) Pa5 (20 μM) | 0.0 | 0.0 | 0.0 | 0.0 |
| 4 | (+) Pa5' (100 μM) | 250.3 | 264.3 | 257.3 | 68.4 |
| (5) MIG (CXCL9) | | | | | |
| 1 | (−) | 344.0 | 233.1 | 288.6 | 37.6 |
| 2 | (+) | 851.8 | 683.5 | 767.7 | 100.0 |
| 3 | (+) Pa5 (20 μM) | 0.0 | 0.0 | 0.0 | 0.0 |
| 4 | (+) Pa5' (100 μM) | 672.8 | 660.1 | 666.4 | 86.8 |
| (6) VEGF (VEGF-A/Vasculotropin) | | | | | |
| 1 | (−) | 1051.2 | 1110.3 | 1080.8 | 132.2 |
| 2 | (+) | 837.3 | 797.4 | 817.4 | 100.0 |
| 3 | (+) Pa5 (20 μM) | 241.4 | 232.3 | 236.8 | 29.0 |
| 4 | (+) Pa5' (100 μM) | 875.1 | 918.4 | 896.7 | 109.7 |
| (7) IL-17 | | | | | |
| 1 | (−) | 0.0 | 0.0 | 0.0 | 0.0 |
| 2 | (+) | 93.3 | 154.4 | 123.9 | 100.0 |
| 3 | (+) Pa5 (20 μM) | 0.0 | 0.0 | 0.0 | 0.0 |
| 4 | (+) Pa5' (100 μM) | 6.1 | 67.2 | 36.7 | 29.6 |
| (8) Thymus Chemokine (CXCL7) | | | | | |
| 1 | (−) | 278.3 | 251.3 | 264.8 | 83.7 |
| 2 | (+) | 318.0 | 315.1 | 316.5 | 100.0 |
| 3 | (+) Pa5 (20 μM) | 0.0 | 0.0 | 0.0 | 0.0 |
| 4 | (+) Pa5' (100 μM) | 62.8 | 83.2 | 73.0 | 23.1 |

Based on the above, it was revealed that Pa5 and Pa5' can inhibit the induction of many inflammatory chemokines/cytokines, and have excellent anti-inflammatory action.

Example 6

The action of inhibiting production of nitrogen monoxide (NO) was examined to investigate the anti-inflammatory action of Pa9.

Figure 5:
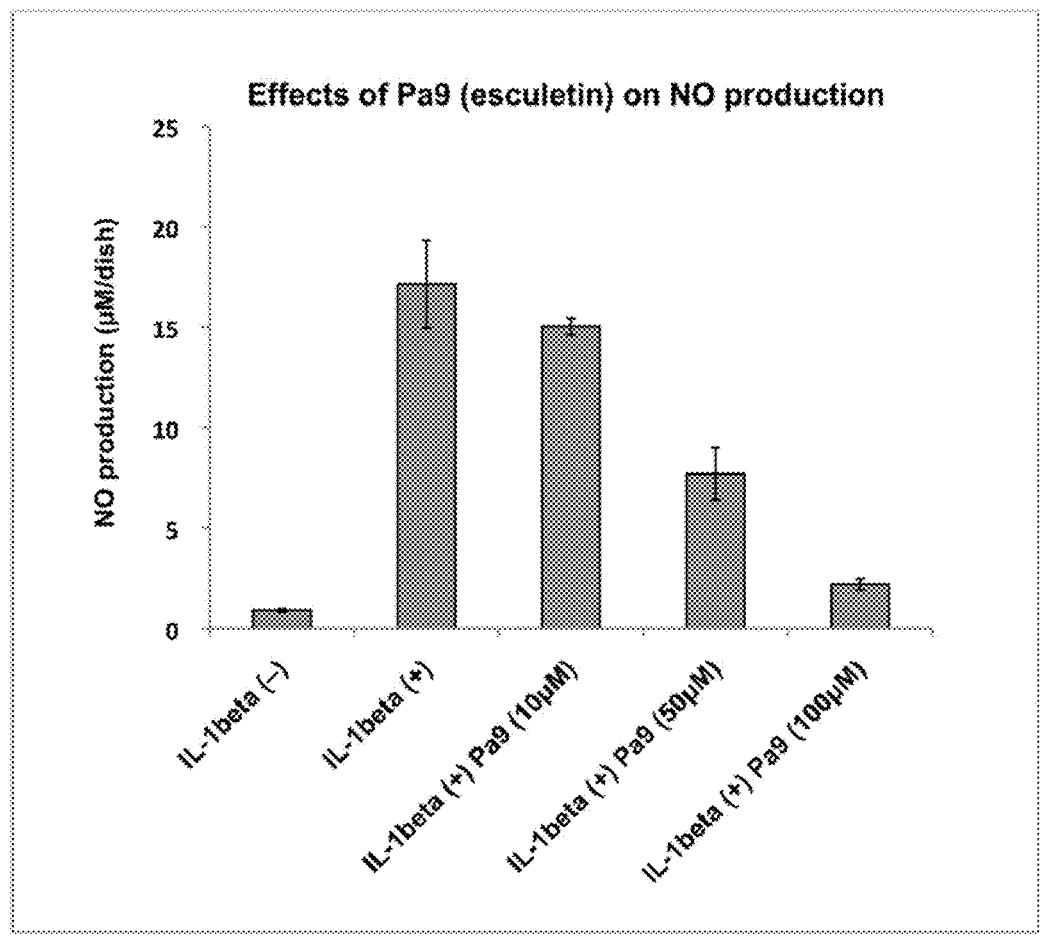
FIG. 5 is a view showing the results of measurement of NO productions.

Liver cells originated from rats were cultured in like manner with Example 4. On day 1 after the start of the culture, the cells were subjected to replacement with fresh WE free of any serum and hormone, and recombinant rat IL-1β (similar to that in Example 4) and Pa9 extracted with methanol in Example 3 were added to the medium. In each medium, the concentration of IL-1β was 1 nM, and the concentrations of Pa9 were 10 μM, 50 μM, and 100 μM (FIG. 5). The amount of NO in each medium was measured 8 hours after the addition of IL-1β and Pa9 in like manner with Example 4.

Figure 6:
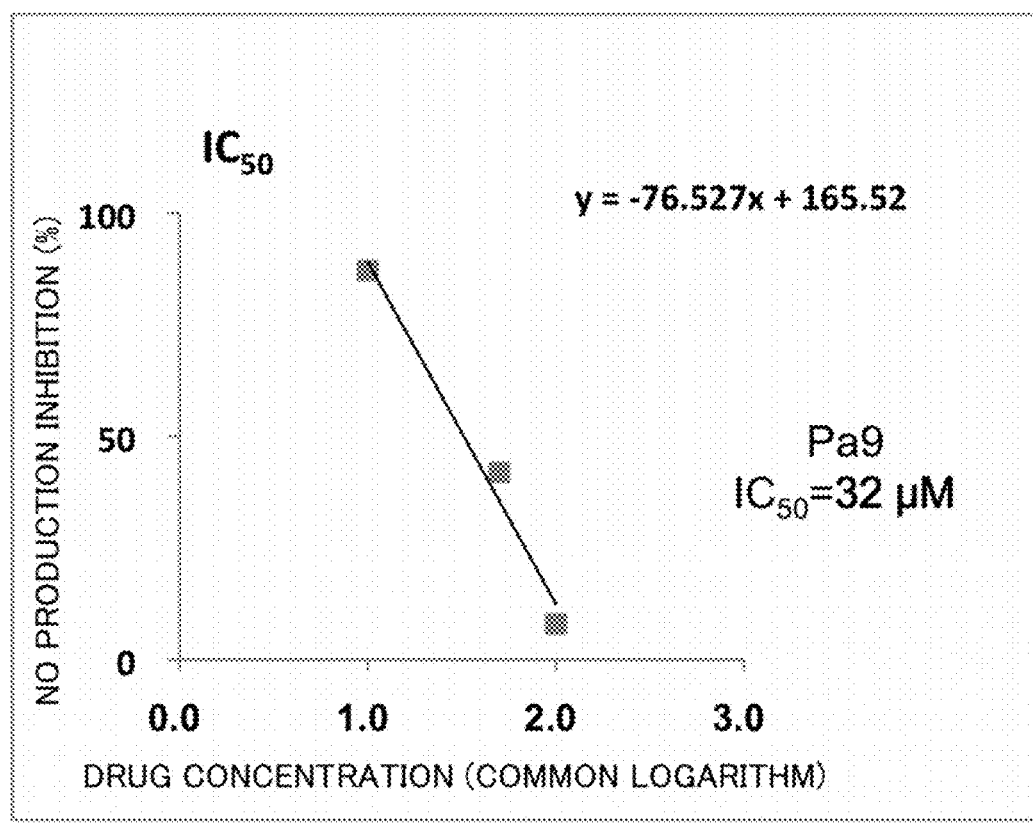
FIG. 6 is a view showing the results of measurement of $IC_{50}$ values.

The results of the measurement of NO productions in the rat liver cells are shown in FIG. 5, and $IC_{50}$ values (drug concentrations at NO production of 50%) are shown in FIG. 6. In FIG. 5, "(−)" means no addition of IL-1β while "(+)" means addition of IL-1β. Pa9 dose-dependently inhibited the production of NO due to IL-1β (FIG. 5). Further, the $IC_{50}$ value of Pa9 was 32 μM (FIG. 6).

Based on the above, it was shown that Pa9 has high NO production inhibitory action. Thus, it was revealed that Pa9 has excellent anti-inflammatory action.

The foregoing describes some example embodiments for explanatory purposes. Although the foregoing discussion has presented specific embodiments, persons skilled in the art will recognize that changes may be made in form and detail without departing from the broader spirit and scope of the invention. Accordingly, the specification and drawings are to be regarded in an illustrative rather than a restrictive sense. This detailed description, therefore, is not to be taken in a limiting sense, and the scope of the invention is defined only by the included claims, along with the full range of equivalents to which such claims are entitled.

The invention claimed is:

1. A method for treating inflammation comprising administering a compound represented by Formula (I), or (II) described below:

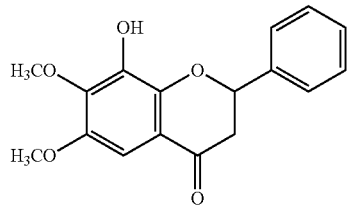

(I)

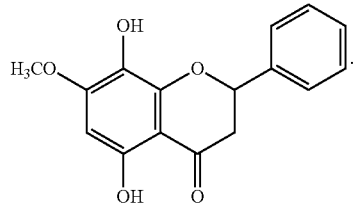

(II)

2. A method for producing a compound represented by Formula (I), (II), or (III) described below:

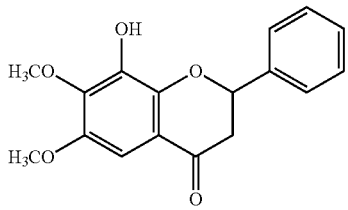

(I)

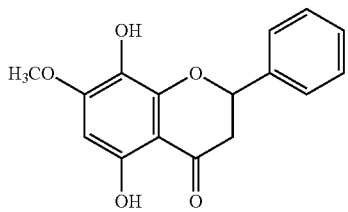

(II)

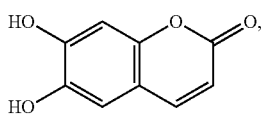

(III)

wherein the method comprises:
a) grinding a part or an entire Lamiaceae plant to obtain a ground product;
b) extracting the ground product with water or an organic solvent at 3 to 121° C. to obtain a liquid solvent extract;
c) concentrating the liquid solvent extract under reduced pressure to obtain a concentrated residue; and
d) fractionating the residue to obtain the compound represented by Formula (I), (II), or (III).

* * * * *